United States Patent
Antonelli et al.

(10) Patent No.: US 7,128,714 B1
(45) Date of Patent: Oct. 31, 2006

(54) NON-CONTACT WAVEFORM MONITOR

(75) Inventors: Lynn T. Antonelli, Cranston, RI (US); John F. Lomba, Pawtucket, RI (US); William J. Ohley, Wakefield, RI (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 403 days.

(21) Appl. No.: 10/748,923

(22) Filed: Dec. 24, 2003

(51) Int. Cl.
*A61B 5/00* (2006.01)

(52) U.S. Cl. .................... 600/485; 600/481
(58) Field of Classification Search ............... 600/485, 600/513, 504, 481
See application file for complete search history.

(56) References Cited

U.S. PATENT DOCUMENTS

| | | | |
|---|---|---|---|
| 4,166,695 A | | 9/1979 | Hill et al. |
| 4,746,211 A | * | 5/1988 | Ruth et al. .................. 356/28.5 |
| 5,280,789 A | | 1/1994 | Potts |
| 5,361,769 A | | 11/1994 | Nilsson |
| 5,363,855 A | * | 11/1994 | Drzewiecki et al. ......... 600/485 |
| 5,778,878 A | * | 7/1998 | Kellam ....................... 600/473 |
| 5,949,546 A | * | 9/1999 | Lee et al. .................... 356/492 |
| 5,954,658 A | * | 9/1999 | Gorti ........................... 600/504 |
| 6,533,729 B1 | * | 3/2003 | Khair et al. ................. 600/503 |
| 2003/0191400 A1 | * | 10/2003 | Shalman et al. ............ 600/486 |
| 2004/0147850 A1 | * | 7/2004 | Amano et al. .............. 600/513 |

* cited by examiner

*Primary Examiner*—Charles A Marmor, II
*Assistant Examiner*—Karen E Toth
(74) *Attorney, Agent, or Firm*—Jean-Paul A. Nasser; James M. Kasischke; Michael P. Stanley

(57) ABSTRACT

A non-contact method and apparatus for continuously monitoring a physiological event in a human or animal, such as blood pressure, which involves utilizing a laser-based interferometer system to produce a waveform that is representative of continuous blood pressure in a subject. The invention may preferably utilize a laser Doppler vibrometer which is oriented to produce a laser beam directed toward the subject substantially perpendicular to a skin surface of the subject wherein the skin surface is moveable in response to blood pressure. The vibrometer is sensitive to motion of the skin surface in a direction parallel to the laser beam and produces a signal representative of this motion. By plotting the velocity of the skin surface movement in the direction parallel to the laser beam with respect to time, a waveform is produced that has been found to be representative of the blood pressure waveform and highly defined to thereby permit accurate timing analysis thereof relating to cardiac cycles.

18 Claims, 3 Drawing Sheets

NON-CONTACT WAVEFORM MONITOR

STATEMENT OF GOVERNMENT INTEREST

The invention described herein may be manufactured and used by or for the Government of the United States of America for governmental purposes without the payment of any royalties thereon or therefore.

CROSS REFERENCE TO OTHER PATENT APPLICATIONS

Not applicable.

BACKGROUND OF THE INVENTION (1) Field of the Invention

The present invention relates generally to a method and apparatus for measuring and monitoring physiological events in humans and animals, and more particularly to a non-contact method and apparatus for continuously measuring and monitoring physiological events in humans or animals using a laser Doppler vibrometer to create waveforms which are directly related to the physiological events.

(2) Description of the Prior Art

For decades, there has been a long felt but unsolved need to continuously and accurately measure physiological events such as blood pressure without making contact with the patient. For many patients, such as burn victims, neonates, and for patients who need to be monitored without disturbing sleep or rest, the ability to accurately monitor blood pressure waveforms without contact has long been desired, but never accomplished.

Invasive monitoring systems, using intra-arterial catheters containing miniature pressure transducers are implemented for continuous monitoring of arterial pressure waveforms, as well as determining blood pressure values throughout the cardiac cycle. However, due to the requirement of inserting these sensors into the arterial system, the patient may be placed in distress.

An extremely well known non-invasive, contact method of measuring blood pressure uses a sphygmomanometer cuff wrapped around the subject's arm above the elbow. As the cuff is being inflated, a stethoscope is utilized to hear the sounds that correspond to the systolic and diastolic end-points. These end-points assist in determining the corresponding blood pressure values. This method provides only systolic and diastolic pressure values for a moment in time and does not provide time-continuous pressure measurements.

Methods for continuously monitoring blood pressure that do not require insertion of sensors into an artery, i.e., non-invasive methods, have been developed within the last decade. For instance, U.S. Pat. No. 5,363,855, which is discussed below, discloses a non-invasive means for continuously monitoring blood pressure. However, contact must be made with the subject and so a non-contact method for measuring blood pressure is not disclosed. Other prior art teachings as listed below, disclose various means for measuring blood flow velocity, blood oxygen saturation, and the like, by non-contact means. However, such techniques are complicated to set up and have not been able to provide sufficient accuracy or definition of the timing of the blood pressure waveform so as to be of any significant benefit in analysis of the cardiac cycle beyond very roughly indicating basic features such as the heart rate. For instance, such techniques have never been utilized to accurately detect the timing of the dicrotic notch within the arterial blood pressure waveform, and may be incapable of doing so.

Continuous recording of an accurate blood pressure waveform permits time series data analysis of the cardiac cycle. Analysis of the arterial pressure waveform identifies important events in the cardiac cycle, e.g., the timing of peak systole, the dicrotic notch, the pre-ejection period (PEP), the left ventricular ejection time (LVET), pulse rate, etc. Information about the systolic time intervals is useful in assessing cardiac condition and various disease states, including left ventricular failure, myocardial infarction, coronary artery disease, and valve disorders.

The time intervals of the various stages of the cardiac cycle are also observed for changes under cardiac disease conditions and pharmacological influence. For example, continuous monitoring of pre-ejection period and left ventricular ejection time ratios may be utilized to test the effects of drugs, exercise, or other stimuli, whereby an increase or decrease in the ratio may indicate an improvement or worsening of systolic efficiency.

The three basic systolic time intervals are the pre-ejection period (PEP), left ventricular ejection time (LVET) and total electromechanical systole (QS2). Linear relationships between heart rate (HR) and the duration of the systolic phases of the left ventricle (LV) have been derived by observation. These following equations have been utilized in the prior art to predict the durations of the systolic time intervals for normal patient observations based on the heart rate alone:

$$PEP = -0.0004 * HR + 0.126 \quad (1)$$

$$LVET = -0.0016 * HR + 0.394 \quad (2)$$

$$QS2 = -0.020 * HR + 0.522 \quad (3)$$

The dicrotic notch as observed on a blood pressure waveform indicates the occurrence of the closure of the aortic valve and marks the end of left ventricular ejection. This event represents the end of the systolic phase and the start of diastole and left ventricular relaxation. The location of the dicrotic notch on a blood pressure waveform can be used for evaluating the above listed linear regression equations that may be utilized to predict the systolic time interval as a function of heart rate. The regression equations are expected to deviate for patients with cardiac dysfunction.

The following U.S. patents describe various prior art systems related to the above discussed problems but do not satisfy the long felt but unsolved need for non-contact blood pressure waveform monitoring.

U.S. Pat. No. 5,778,878, issued Jul. 14, 1998, to K. Kellam, discloses a laser Doppler technique to determine the velocity of blood cells in skin or other tissue capillaries. A laser beam is focused on to a capillary by means of a lens, mirror and beam splitter system. Measurement of the velocity of the blood cells in a direction substantially perpendicular to the surface of the tissue is effected by detecting directly back-scattered radiation.

U.S. Pat. No. 5,363,855, issued Nov. 15, 1994, to Drzewiecki et al., discloses a pressure waveform monitor that noninvasively monitors the pressure waveform in an underlying vessel such as an artery. The apparatus comprises at least one continuous, relatively thin and narrow diaphragm mounted in a housing to be placed on the tissue overlying the vessel of interest. The diaphragm is longer than the diameter of the vessel for purposely monitoring pressure in the tissue adjacent to the vessel of interest. The device also comprises deformation sensor means for measuring deformation of the diaphragm both over the vessel and adjacent to the vessel, and signal processing means for combining the waveform of the vessel as monitored by the part of the diaphragm over the vessel with the waveforms of adjacent tissue to accurately determine the actual pressure waveform in the vessel.

U.S. Pat. No. 5,361,769, issued Nov. 8, 1994, to G. Nilsson discloses a method and a system for reducing the distance-dependent amplification factor when measuring fluid flow movements with the aid of an image-producing laser-Doppler technique, in particular when measuring blood perfusion through tissue. A laser beam source directs a laser beam onto a measurement object, which scatters and reflects the beam. The reflected light is received by a detector that senses the broadening in frequency caused by the Doppler effect. One or more lenses are placed in the path of the beam and are intended to maintain constant the number of coherence areas on the detecting surface of the detector and independent of the distance between detector and measurement object.

U.S. Pat. No. 5,280,789, issued Jan. 25, 1994, to R. A. Potts, discloses an apparatus for vertically aligning a given point on a pressure transducer unit with a desired point on a patient comprising a light source, a housing adapted to contain the light source, and at least one leveling tube having a leveling axis that is substantially parallel to the light beam. The leveling tube comprises a closed transparent envelope containing a liquid and a bubble of gas, and lines formed on the envelope, where the leveling axis is substantially horizontally aligned when the bubble of gas is located between the two lines. The apparatus includes an indicating mark formed on the housing means where the beam of light is vertically aligned with the given point on the transducer. A locking system selectively locks the housing means to prevent movement thereof relative to the transducer unit when the beam of light is both horizontally aligned and vertically aligned with the given point on the transducer unit. To vertically align the given point with the desired point, one of the transducer units and the patient are vertically displaced relative to the other until the light source causes light to reflect off of the patient at the desired point.

U.S. Pat. No. 4,166,695, issued Sep. 4, 1979, to Hill et al., discloses a means for measuring blood flow in retinal blood vessels by directing laser radiation along an optical path into the eye and onto a blood vessel. Laser radiation reflected off moving blood corpuscles is directed back along the optical path and into a detector. This reflected laser radiation is mixed with a proportion of the original laser signal to determine the Doppler shift produced by the moving blood corpuscles and hence blood velocity.

U.S. Pat. No. 5,995,856, issued Nov. 30, 1999, to Mannheimer et al., discloses monitoring of physiological parameters of a patient through the use of optical systems that do not require direct physical contact with the patient. The method and apparatus relate primarily to pulse oximetry for monitoring pulse rate and arterial blood oxygen saturation. However, the apparatus and method of this invention are applicable to any form of optical detection of the physiological parameters in which light of any wavelength, visible or invisible, is directed from a remote instrument into a patient at a first imaging site, and subsequently collected at a second site spaced from the first site.

U.S. Pat. No. 6,007,494, issued Dec. 28, 1999, to Zenner et al., discloses a device for determining data on auditory capacity wherein the device preferably has non-contact means for measuring vibrations of the middle-ear ossicles and/or the tympanic membrane by means of electromagnetic waves. The electromagnetic waves used for the measurement are input by means of a microscope, in particular an optical microscope. This microscope can be modular in design, and a module can be provided for the input of a laser beam. The invention also concerns a method of determining data on auditory capacity wherein the method calls for the vibration of the middle ear and/or the eardrum to be measured by means of electromagnetic waves and, from the measurement signals thus obtained, the contributions to the total signal by the middle ear and/or the eardrum determined in at least one processing step.

The Journal of Biomedical Engineering, 4(2): 142–8, 1982, by Brown et al. teaches that a rather complex light emitting diode sensor (LED) has sufficient resolution to detect an arterial pulse.

The above-discussed systems do not disclose a convenient and completely non-contact means for accurately and continuously monitoring blood pressure or creating blood pressure waveforms. Consequently, those skilled in the art will appreciate the present invention that addresses the above and other problems.

SUMMARY OF THE INVENTION

It is a general purpose and object of the present invention to provide an improved non-contact blood pressure waveform monitoring apparatus and method.

Another object is to provide a laser-based system that may be utilized to continuously provide highly detailed information about the timing characteristics of the blood pressure waveform.

Another object is to provide a system that does not require elaborate adjustments of one or more lasers and laser detectors so that the system may be quickly utilized.

These and other objects, features, and advantages of the present invention will become apparent from the drawings, the descriptions given herein, and the appended claims. However, it will be understood that the above listed objects and/or advantages of the invention are intended only as an aid in understanding aspects of the invention, are not intended to limit the invention in any way, and do not form a comprehensive list of objects, features, and advantages.

Accordingly, a non-contact method and apparatus for continuously measuring a blood pressure waveform is provided which may comprise, for example, utilizing a laser based measurement system mounted in a spaced relationship with respect to a subject and directing a laser beam toward a section of the subject's skin surface orienting the laser beam such that it is substantially perpendicular to the skin surface at a location wherein the skin surface is moveable in response to a blood pressure pulse, and/or detecting one or more variables related to movement of the skin surface, and/or producing a blood pressure waveform representation by plotting the one or more variables related to movement of the skin surface.

The non-contact method and apparatus may further comprise use of detectors capable of detecting the one or more variables related to movement of the skin surface in a direction substantially parallel to the laser beam and/or producing the blood pressure waveform representation by plotting skin surface velocity with respect to time through the use of a signal processor.

In one embodiment, the non-contact method and apparatus may comprise utilizing interferometers and interferometer techniques for detecting the one or more variables related to movement of the skin surface. One advantage of the invention is that the apparatus may comprise a single housing to support the means for measuring the blood pressure waveform, i.e., the means to effect steps such as directing of the laser beam to the skin surface and the detecting of the reflected laser beam.

The non-contact method may further comprise analyzing the blood pressure waveform representation to determine systolic time interval parameters and/or analyzing the blood pressure waveform parameters to determine heart rate and/or comparing systolic time interval parameters estimated utilizing the heart rate with systolic time interval parameters determined from the blood pressure waveform.

If desired, the non-contact method may also be utilized to measure other physiological events such as respiration to the extent that a skin surface is moveable in response to such a physiological event.

BRIEF DESCRIPTION OF THE DRAWINGS

A more complete understanding of the invention and many of the attendant advantages thereto will be readily appreciated as the same becomes better understood by reference to the following detailed description when considered in conjunction with the accompanying drawings, wherein like reference numerals refer to like parts and wherein.

DESCRIPTION OF THE PREFERRED EMBODIMENT

The present invention provides a non-contact method and apparatus for continuously monitoring physiological events such as the anatomical blood pressure waveform with sufficient accuracy and precision to determine important timing related parameters such as, for example, the left ventricular ejection time (LVET) and pre-ejection period (PEP). For cardiac cyclic timing diagnostic purposes, the timing of the blood pressure waveforms should be measured with sufficient accuracy so that the components of the waveform, e.g., the dicrotic notch, are available for accurate analysis. However, it has been observed by the inventors that cardiac cyclic analysis of the blood pressure waveform does not require absolute values of blood pressure. Thus, while the present technique does not necessarily directly measure or provide absolute values of blood pressure, cyclic analysis of the blood pressure waveform can be readily performed utilizing the data produced by the present invention. Calibration techniques may be utilized as discussed hereinafter to provide absolute values in certain circumstances, if desired.

Figure 1:
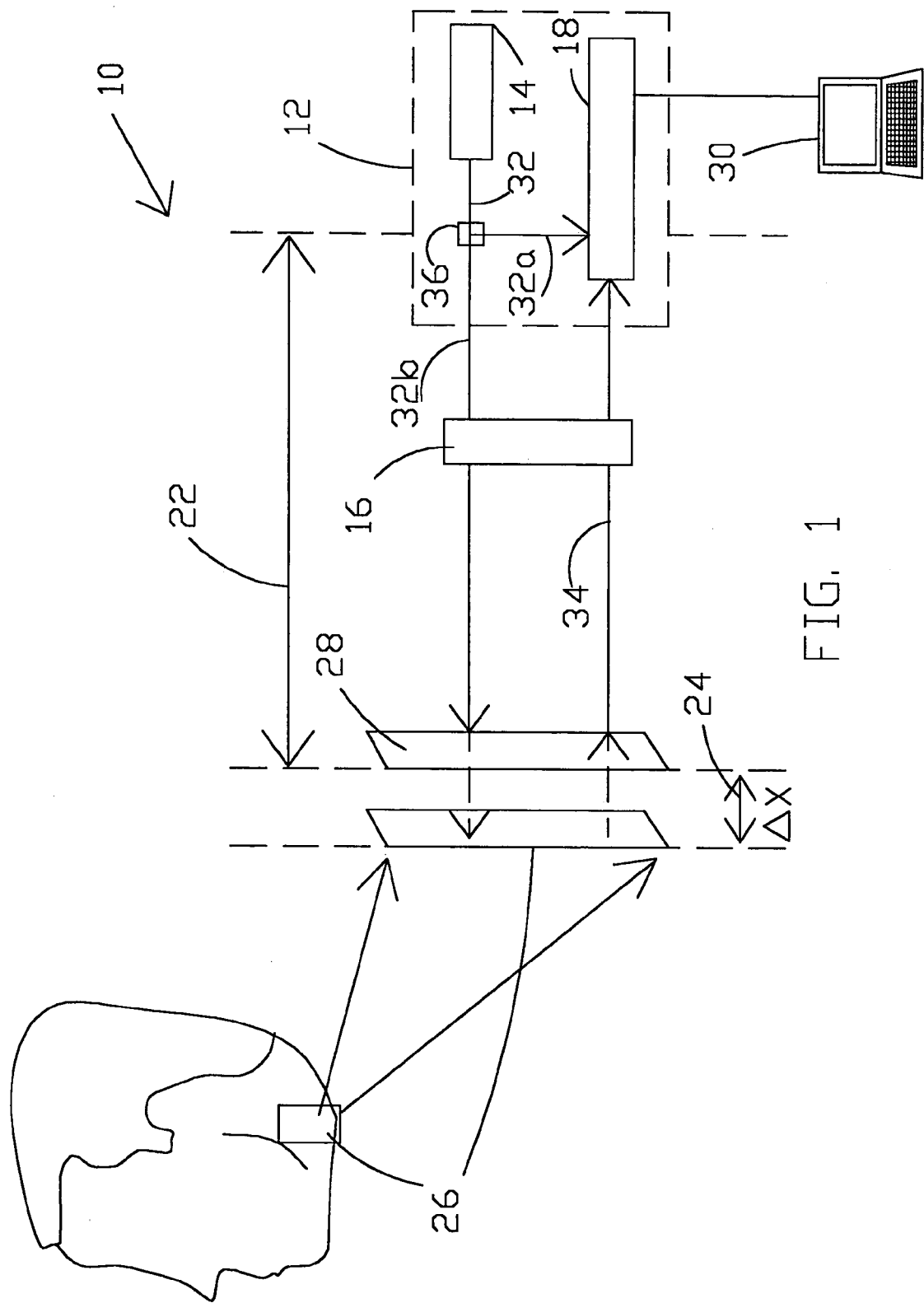
FIG. 1 is a schematic overview of the operation and setup of a non-contact blood pressure waveform monitoring system in accord with one embodiment of the present invention.

Referring now to the drawings and, more particularly, to FIG. 1, there is shown a non-contact blood pressure waveform monitoring system 10 in accord with a preferred embodiment of the present invention. System 10 utilizes laser Doppler vibrometer 12 to detect the movement of skin on a patient, in this case the skin surface 26 above the carotid artery.

Laser Doppler vibrometer 12 comprises laser source 14 capable of emitting a laser beam 32 that travels the distance 22 from laser source 14 to skin surface 26. The laser beam is preferably directed perpendicularly or substantially perpendicularly to skin surface 26. Blood flowing through the carotid artery directly below the skin causes skin surface 26 to pulsate in a rhythm corresponding to ventricular contractions of the patient's heart. Skin surface 26 moves an amount $\Delta x$, as indicated by numeral 24, from its initial position to a position represented by plane 28. $\Delta x$ represents the distance of movement of the plane of skin surface 26 in a direction substantially parallel to the laser beam produced by laser source 14. Laser light is reflected by skin surface 26. The reflected laser beam 34 is focused by lens 16 and recovered by detector 18. The reflected laser light beam 34 is modulated by the movement of skin surface 26 by means of a Doppler shift in the optical wavelength, as compared to the original laser beam 32 produced by laser 14. Detector 18 determines the velocity of the pulsatile skin motion as derived from the Doppler shift.

Detector 18 preferably comprises an interferometer for comparison of the initially produced laser beam (or a reference beam derived there from) with the reflected laser beam. In a preferred embodiment, laser Doppler vibrometer 12 operates by splitting the laser beam 32 with a beam splitter 36 into a reference beam 32$a$ and a sensing beam 32$b$. The reference beam 32$a$ is frequency shifted by a modulator (not shown) in detector 18 so that the components of detector 18 can discriminate between the reflected laser beam 34 with the Doppler modulation and the reference beam 32$a$. Detector 18 measures the Doppler frequency of the reflected beam 34 as modulated by the movement of skin surface 26. The maximum and therefore optimum reflected signal occurs when laser Doppler vibrometer 12 is oriented such that the laser beam 32 produced by laser source 14 is substantially perpendicular to skin surface 26.

Detector 18 generates a continuous stream of analog output voltages corresponding to the pulsation velocity of skin surface 26. The analog voltage signals may be fed to computer 30 where the analog voltage signals are digitized, recorded, and analyzed as desired. Alternatively, the analog voltage may be fed to a device, such as an oscilloscope for immediate display of the blood pressure waveform.

Figure 2:
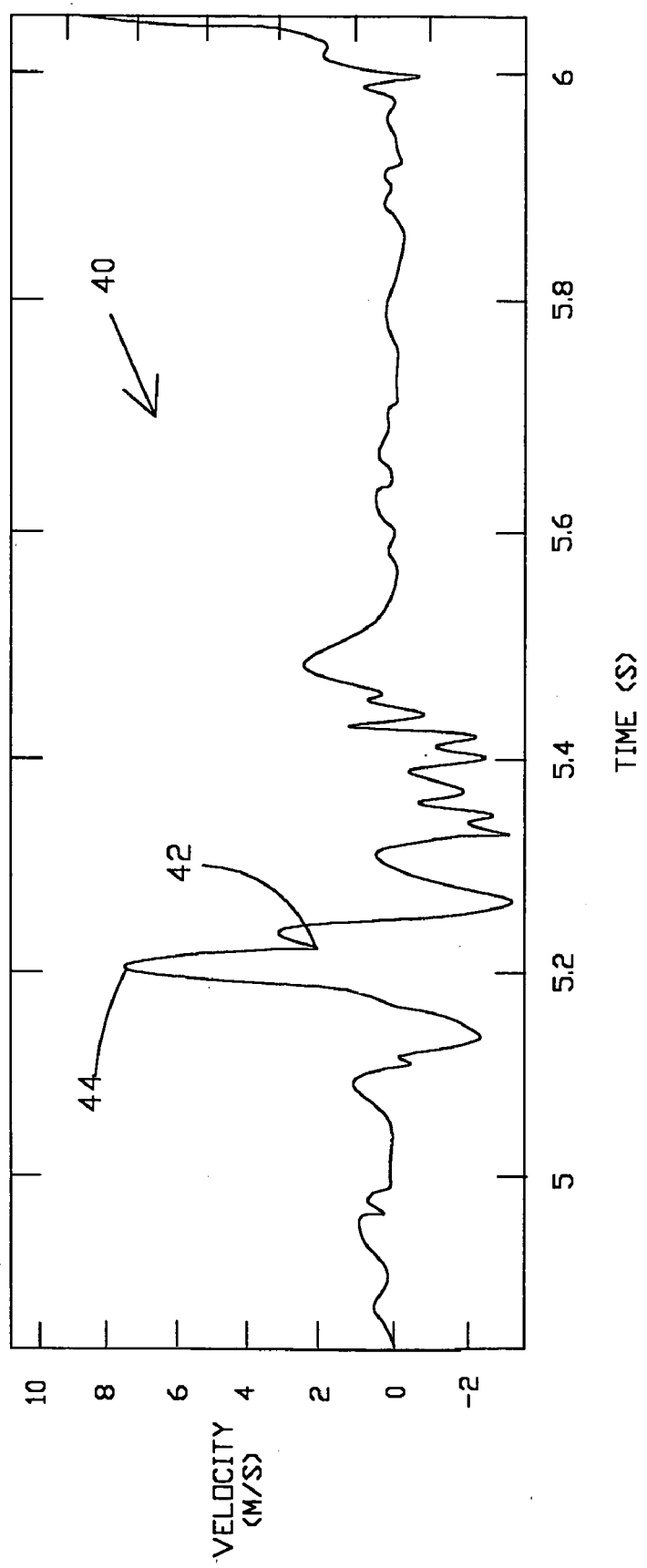
FIG. 2 is a graph of a blood pressure waveform obtained by measuring skin velocity in accord with the present invention for a single cardiac cycle.
Figure 3:
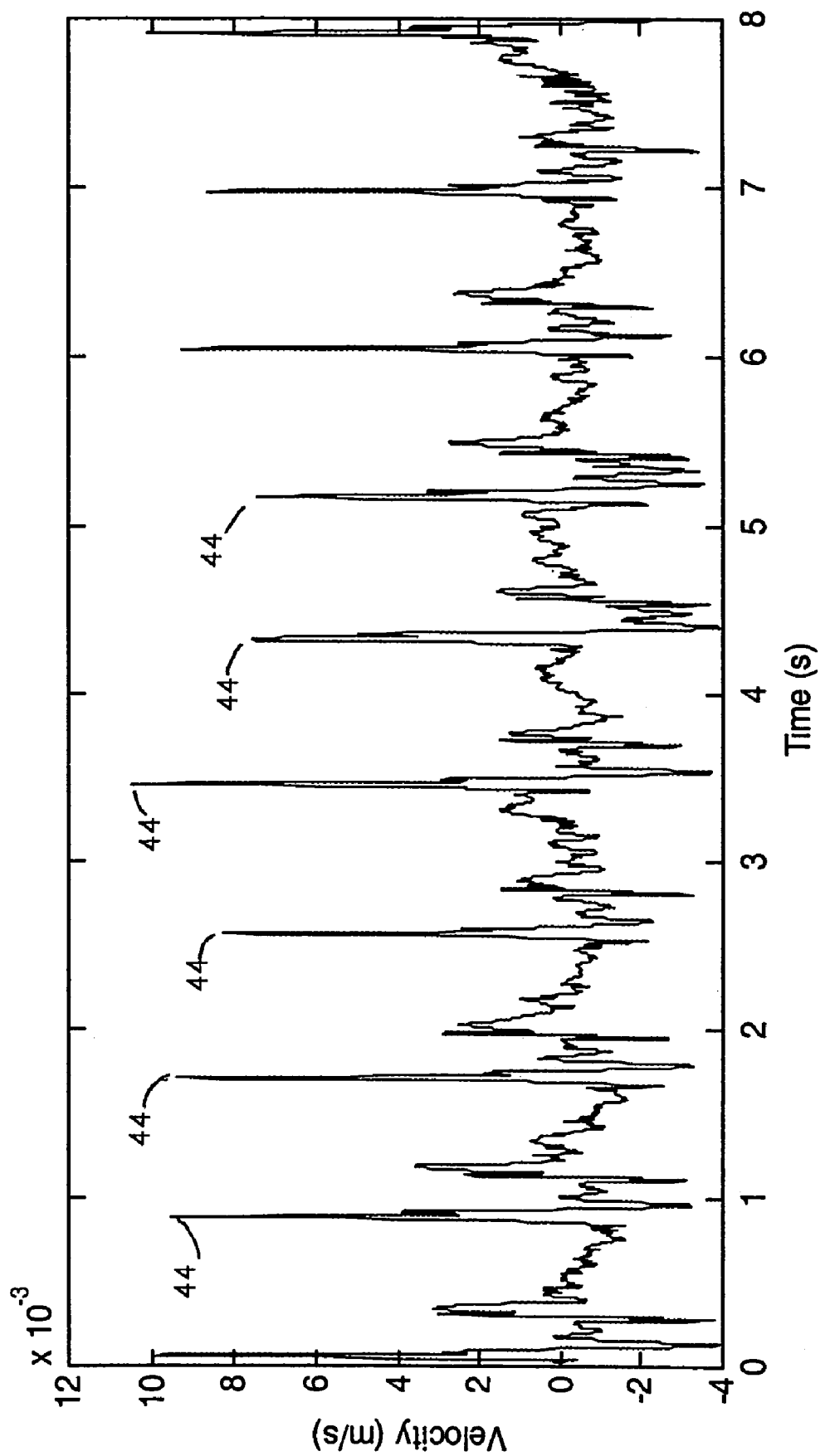
FIG. 3 is a graph of a blood pressure waveform obtained by continuously measuring skin velocity for several cardiac cycles in accord with the present invention.

Utilizing the pulsation velocity of skin surface 26 over time, computer 30 can plot a highly accurate representative blood pressure waveform 40 as indicated in FIG. 2. Such a waveform is highly suitable for cardiac cyclic analysis. For instance, dicrotic notch 42, which indicates the closing of the aortic valve, is plainly visible as is the peak systole 44. Heart rate is easily determined by timing the distance between the easily distinguishable peaks of successive pulse waveforms as indicated in FIG. 3, which shows multiple peak systole 44 over a period of time. Once heart rate is determined, the PEP, LVET and QS2 can be derived from formulae (1), (2) and (3) as indicated above. Thus, while the present invention does not directly measure arterial pressure, nonetheless it has been found by the inventors that the blood pressure waveform so obtained is quite suitable for timing analysis of the cardiac cycle to thereby evaluate cardiac function with timing events such as the systolic peak 44 and dicrotic notch 42.

It will be noted that all of the components of the laser Doppler vibrometer 12, including the laser source 14, the lens 16, and the detector 18, are preferably built into a single housing and are therefore more easily and quickly set up than prior art laser sensor instruments discussed herein. Moreover, suitable laser Doppler vibrometers are commercially available so that after review of the specification herein, one of skill in the art will be able to practice the invention.

The arterial pressure waveform 40 obtained by laser Doppler vibrometer 12 may be analyzed to obtain various waveform characteristics. The timing of these waveforms may be combined with an electrocardiogram signal to estimate systolic time interval parameters. Alternatively, the systolic time interval may be estimated using heart rate information from the recorded waveform and applied to regression equations (1), (2), and (3).

While absolute blood pressures are not available directly from the present invention, such readings may be obtained by calibration techniques as described below. For example, a patient to be monitored during sleep may have the maximum/minimum blood pressures directly measured by existing contact means while awake to thereby calibrate the blood pressure waveform that is produced in accord with the present invention. Statistical techniques relating to expansion distances directly measured may be determined to estimate blood pressures in normal patients such as based on the amplitude of the movement parameters. Thus, the present invention might also be utilized to predict abnormalities due to deviations from anticipated values of absolute blood pressures determined statistically.

While similar but technically different in some ways, the terms laser Doppler vibrometer, laser Doppler velocimeter, and laser interferometer are used somewhat interchangeably herein and may each be utilized in accord with the present invention. For instance, the laser Doppler velocimeter is also sometimes utilized to measure the velocity of objects in the direction perpendicular to the laser beam and may therefore be utilized by itself or in conjunction with a laser Doppler vibrometer to measure the expansion of the artery by means of monitoring the subsequent effect on the skin surface.

The present invention may also be utilized to provide waveforms related to movement of any portion of the body that moves and to record any physiological parameters using a laser Doppler vibrometer containing a laser interferometer inherent to its design.

In summary, the present invention utilizes a laser beam 32 produced by laser 14 to measure the movement of a particular skin surface area, such as skin surface 26 adjacent to any artery, such as the carotid artery. The invention detects the movement and plots the velocity of skin movement versus time to create a waveform of the physiological event corresponding to the skin movement such as the arterial blood pressure.

Many additional changes in the details, materials, steps and arrangement of parts, herein described and illustrated to explain the nature of the invention, may be made by those skilled in the art within the principle and scope of the invention. For example, it may be desirable to utilize a fiber optic means for directing and/or detecting the laser beams of interest. Due to the motion of a patient's skin surface, which is not directly related to the measurement of the biological signal of interest, e.g., blood pressure waveform, an adaptive focus may be utilized to maintain the interrogating laser beam on the desired measurement area, such as the carotid artery.

It is therefore understood that within the scope of the appended claims, the invention may be practiced otherwise than as specifically described.

What is claimed is:

1. An apparatus for continuously measuring a physiological event of a subject, comprising:
    a laser source capable of directing a laser beam toward the subject that will reflect said laser beam at a skin region of the subject wherein said skin region is moveable in response to said physiological event; and
    a detector comprising a laser interferometer that employs interferometer techniques to detect said reflected laser beam and determine at least a velocity of said skin surface at a given moment in time.

2. The apparatus of claim 1, further comprising a processor joined in communication with said detector for analyzing said velocity with respect to time thereby analyzing said physiological event.

3. The apparatus of claim 1, further comprising a single housing to contain said laser source and said detector.

4. The apparatus of claim 2, wherein said processor produces a waveform representation of said physiological event by plotting said velocity of said skin surface with respect to time and further comprising:
    a means for displaying said velocity with respect to time thereby displaying said physiological event.

5. The apparatus of claim 4, wherein said physiological event is a blood pressure of the subject and wherein said waveform representation is representative of a blood pressure waveform and contains dicrotic notch information.

6. The apparatus of claim 4, wherein said physiological event is a rate of respiration of the subject.

7. The apparatus of claim 5, wherein said processor analyzes said blood pressure to determine systolic time interval parameters.

8. The apparatus of claim 5, wherein said processor analyzes said blood pressure to determine heart rate.

9. The apparatus of claim 8, wherein said processor compares systolic time interval parameters estimated utilizing said heart rate with systolic time interval parameters determined from said blood pressure.

10. A method for continuously measuring a physiological event of a subject, comprising:
    directing a laser beam toward a skin surface of said subject that will reflect said laser beam wherein said skin surface is moveable in response to said physiological event;
    detecting said reflected laser beam by utilizing a laser interferometer and interferometer techniques for detecting said reflected laser beam and through said detection determining said one or more variables related to movement of said skin surface;
    determining at least one variable related to movement of said skin surface; and
    analyzing said at least one variable related to movement of said skin surface thereby producing a metric concerning said physiological event.

11. The method of claim 10, wherein said physiological event is blood pressure.

12. The method of claim 10, wherein said physiological event is respiration.

13. The method of claim 10, wherein the metric concerning said physiological event is the velocity of said skin surface.

14. The method of claim 10, further comprising displaying said metric concerning said physiological event.

15. The method of claim 13, wherein said physiological event is a blood pressure and further comprising the step of producing a blood pressure waveform representation containing dicrotic notch information by plotting skin surface velocity with respect to time.

16. The method of claim 15, further comprising the step of analyzing said blood pressure waveform representation to determine systolic time interval parameters.

17. The method of claim 15, further comprising the step of analyzing said blood pressure waveform parameters to determine heart rate.

18. The method of claim 17, further comprising the step of comparing systolic time interval parameters estimated utilizing said heart rate with systolic time interval parameters determined from said blood pressure waveform.

* * * * *